United States Patent [19]

Puckette

[11] Patent Number: 5,021,380

[45] Date of Patent: Jun. 4, 1991

[54] CATALYST FOR PREPARATION OF BIARYL COMPOUNDS

[75] Inventor: Thomas A. Puckette, Longview, Tex.

[73] Assignee: Eastman Kodak Company, Rochester, N.Y.

[21] Appl. No.: 492,017

[22] Filed: Mar. 12, 1990

Related U.S. Application Data

[62] Division of Ser. No. 346,769, May 3, 1989, Pat. No. 4,939,309.

[51] Int. Cl.$^5$ ................................................ C08F 4/70
[52] U.S. Cl. .................................... 502/107; 502/104; 502/109; 502/113; 502/117
[58] Field of Search ............... 502/104, 109, 107, 113, 502/117

[56] References Cited

U.S. PATENT DOCUMENTS

| | | | |
|---|---|---|---|
| 4,000,211 | 12/1976 | Smith et al. ................ | 502/117 X |
| 4,187,197 | 2/1980 | Kabanov et al. ............ | 502/117 |
| 4,263,466 | 4/1981 | Colon et al. ................. | 502/162 X |
| 4,283,305 | 8/1981 | Chauvin et al. ............. | 502/117 |
| 4,533,651 | 8/1985 | Masters et al. .............. | 502/117 |

*Primary Examiner*—Patrick P. Garvin
*Attorney, Agent, or Firm*—J. Frederick Thomsen; William P. Heath, Jr.

[57] ABSTRACT

A method for the preparation of biaryl compounds is disclosed which comprises contacting an aryl halide with a tertiary-alkyl organometallic reagent (or the precursor components thereof) in the presence of a catalyst comprising a nickel compound and a coordinating ligand under conditions suitable for the formation of biaryl compound.

In an alternate embodiment of the present invention, nickel(O) compounds are prepared from nickel(II) compounds by contacting a nickel(II) compound with a combination of an organophosphine and a bidentate nitrogen-containing coordinating ligand, and a tertiary-alkyl organometallic reagent (or the precursor components thereof) in an aprotic, non-polar, ether-containing solvent system for a time and under conditions suitable for the formation of nickel(O) compound.

9 Claims, No Drawings

CATALYST FOR PREPARATION OF BIARYL COMPOUNDS

This is a divisional of copending application Ser. No. 07/346,769 filed on May 3, 1989 and now U.S. Pat. No. 4,939,309.

DESCRIPTION

The present invention relates to the preparation of biaryl compounds from aryl halides. In a particular aspect, the present invention relates to the reductive coupling of aryl halides.

BACKGROUND OF THE INVENTION

It is known that biphenyl compounds can be produced by the reductive coupling of aryl halides. For example, Colon, et al., in U.S. Pat. No. 4,263,466, disclose the use of a metallic reducing agent such as zinc, magnesium, or manganese in a dipolar, aprotic solvent such as dimethylformamide with a catalyst containing a nickel compound in combination with organophosphines and alkali metal halide promoters. The reducing metal converts the nickel salts into highly reactive zerovalent nickel compounds which promote the coupling of the aryl halides and regenerate the nickel salts which can be reduced again to the zerovalent state, thereby maintaining the catalytic cycle.

Chao, et al., Journal of Organic Chemistry, Volume 48 pages 4904-4907 (1983), disclose a similar approach wherein aryl halides are reacted with an equivalent amount of a highly activated metal such as nickel powder.

An alternative approach is to activate an aryl halide by a chemical transformation, and then allow the activated aryl halides to couple to form biaryls species. For example, Gilman, et al., in the Journal of the American Chemical Society, Volume 61, pages 957-959 (1939), demonstrated this approach by the reaction of two equivalents of aryl Grignard reagents with one equivalent of nickel (II) salts to give biaryl compounds. This reaction is believed to proceed through the bis aryl nickel species which then decomposes to give the desired biaryl product.

More recently, Kumada, et al., in Bulletin of the Chemical Society of Japan, Volume 49, pages 1958-1969 (1976), have demonstrated that aryl halides can be reacted with a variety of aliphatic Grignard reagents to give alka-aryl products. In this example, the aliphatic radical reacts with the aryl moiety and becomes bonded thereto.

Since aryl halides are readily available compounds, and the resulting biaryl compounds which can be prepared therefrom find a variety of uses, it would be desirable to find alternate means to promote the coupling of aryl halides to produce high yields of biaryl compounds.

STATEMENT OF THE INVENTION

In accordance with the present invention, it has been found that aryl halides can be reductively coupled to produce biaryl compounds in high yield. By contacting an aryl halide with a tertiary-alkyl (alternatively designated throughout the specification as "t-alkyl") organometallic reagent under reductive coupling conditions, high yields of biaryl compounds are obtained.

The invention method also makes possible the preparation of nickel(0) species from nickel(II) species. This is accomplished by contacting a nickel(II) species with an organophosphine and a bidentate ligand containing at least one nitrogen atom in the presence of a tertiary-alkyl organometallic reagent under conditions suitable for the reduction of nickel.

The practice of the present invention allows for the ready preparation of biaryl derivatives from aryl halide starting materials, including aryl chlorides. Aryl chlorides are generally preferred starting materials as they are more accessible on a commercial basis and are generally less expensive than the corresponding aryl bromides or aryl iodides.

DETAILED DESCRIPTION OF THE INVENTION

In accordance with the present invention, there is provided a method for the preparation of biaryl compounds of the structure:

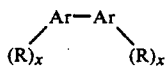

wherein Ar is an aromatic moiety having in the range of 4 up to 20 carbon atoms, each R is independently selected from the group consisting of:
- hydrocarbyl substituents having in the range of 1 up to 20 carbon atoms,
- —OR', wherein R' is a hydrocarbyl radical having in the range of 1 up to 20 carbon atoms, and
- protected carbonyl-containing derivatives thereof, wherein x is an integer falling in the range of 0 up to 8, depending on the size of the aromatic ring (i.e., Ar).

The invention method comprises contacting an aryl halide having the structure:

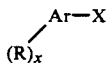

wherein Ar, R and x are as defined above and X is a halogen; with a catalyst system comprising:
(i) a nickel compound,
(ii) an organophosphine ligand,
(iii) a tertiary-alkyl organometallic compound of the structure:

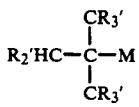

wherein each R' is independently selected from H or alkyl groups having in the range of 1 up to 20 carbon atoms, and M is selected from Li, Na, K, or MgX, wherein X is a halogen, and
(iv) optionally, a bidentate ligand containing at least one nitrogen atom;

wherein said contacting is carried out in a substantially anhydrous, non-polar, ethereal solvent system, optionally containing up to 95 volume percent of an aliphatic or aromatic hydrocarbon diluent at a temperature in the range of about 0° up to 100° C. for a time in the range of about 0.5 up to 24 hours.

In accordance with an alternate embodiment of the present invention, the catalyst system used to promote the invention coupling method comprises the individual components from which the tertiary alkyl organometallic compound can be generated in situ. Thus, the catalyst system alternatively comprises:
(i) a nickel compound,
(ii) an organophosphine ligand,
(iii) a tertiary-alkyl halide of the structure:

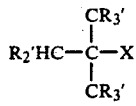

wherein each R' is independently selected from H or alkyl groups having in the range of 1 up to 20 carbon atoms, and X is a halogen,
(iv) a metal, M, selected from Li, Na, K or Mg, and
(v) optionally, a bidentate ligand containing at least one nitrogen atom.

In accordance with another alternate embodiment of the present invention, there is further provided a method for the preparation of a nickel (0) species from nickel (II) compounds comprising contacting a nickel (II) compound with
(i) an organophosphine ligand,
(ii) a bidentate ligand containing at least one nitrogen atom, and
(iii) a tertiary-alkyl organometallic compound of the structure:

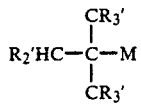

wherein each R' is independently selected from H or alkyl groups having in the range of 1 up to 20 carbon atoms, and M is selected from Li, Na, K, or MgX, wherein X is a halogen,
wherein said contacting is carried out in a substantially anhydrous, non-polar, ethereal solvent system, optionally containing up to 95 volume percent of an aliphatic or aromatic hydrocarbon diluent at a temperature in the range of about 0 up to 100° C. for a time in the range of about 0.5 up to 24 hours.

In accordance with yet another alternate embodiment of the present invention, the combination employed to promote the formation of nickel (0) species from nickel (II) compounds comprises:
(i) an organophosphine ligand,
(ii) a bidentate ligand containing at least one nitrogen atom,
(iii) a tertiary-alkyl halide of the structure:

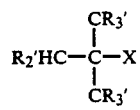

wherein each R' is independently selected from H or alkyl groups having in the range of 1 up to 20 carbon atoms, and X is a halogen, and
(iv) a metal, M, selected from Li, Na, K or Mg.

Aryl halides contemplated for use in the practice of the present invention are compounds having the general structure:

wherein Ar is an aromatic moiety having in the range of 4 up to 20 carbon atoms, each R is independently selected from the group consisting of:
hydrocarbyl substituents having in the range of 1 up to 20 carbon atoms,
—OR', wherein R' is a hydrocarbyl radical having in the range of 1 up to 20 carbon atoms, and
protected carbonyl-containing derivatives thereof; and
wherein X is halogen; and x is an integer falling in the range of 0 up to 8, depending on the size of the aromatic ring (i.e., Ar).

Exemplary aryl halides contemplated for use in the practice of the present invention include:

2-chlorotoluene,
2-bromotoluene,
4-chlorotoluene,
4-bromotoluene,
2-chloro-4-methylnaphthalene,
2-bromo-4-methylnaphthalene,
4-chloroanisole,
4-bromoanisole,
2-chlorobenzyl(2-methoxy)ethyl ether,
2-bromobenzyl(2-methoxy)ethyl ether,
2-chlorobenzyl methyl ether,
2-bromobenzyl methyl ether,
2-chlorobenzyl ethyl ether,
2-bromobenzyl ethyl ether, and the like, as well as mixtures of any two or more thereof.

Tertiary-alkyl organometallic compounds contemplated for use in the practice of the present invention are compounds having the structure

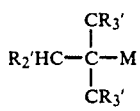

wherein each R' is independently selected from H or alkyl groups having in the range of 1 up to 20 carbon atoms; M is selected from Li, Na, K, or MgX; and wherein X is a halogen.

Exemplary compounds which satisfy the above structural formula include t-butylmagnesium chloride, t-butyl lithium, t-butyl sodium, t-butyl potassium, t-amylmagnesium chloride, t-amyl lithium, t-amyl sodium, t-amyl potassium, and the like.

A wide range of nickel compounds are suitable for use in the practice of the present invention, so long as the nickel compounds employed are essentially water-free. The nickel(II) halide salts are a convenient source of nickel as such compounds are readily available in anhydrous form. Alternatively, hydrates of such compounds can be employed where appropriate means for removal of water, e.g., azeotropic distillation, is employed prior to contacting of the nickel species with tertiary-alkyl organometallic compound. Those of skill in the art recognize that a wide variety of other nickel compounds can be used, e.g., nickel nitrates, sulfates, phosphates, oxides, carbonates, carboxylates, acetylacetonate and the like, as well as Ni(O) complexes such as, for example, bis(1,5-cyclooctadienyl)nickel(O), nickel-(O)tetracarbonyl, and the like.

The nickel(II) halides are presently preferred because of their ready availability in anhydrous form, or ease of preparation in substantially anhydrous form from the hydrated species.

Organophosphines contemplated for use in the practice of the present invention are compounds of the structure:

PR$_3''$ or R$_2''$P-Y-PR$_2''$ wherein each R" is independently selected from the group consisting of hydrocarbyl substituents having in the range of 1 up to 20 carbon atoms, alkoxy moieties, aryloxy moieties, and the like, as well as substituted derivatives thereof, wherein substituted derivatives are selected from ethers, amines, amides, sulfonic acids, esters, hydroxyl groups or alkoxy groups; and Y is selected from alkylene, alkenylene, arylene, biarylene, and the like bridging groups having in the range of 1 up to 30 carbon atoms.

Exemplary organophosphines include triphenylphosphine, tricyclohexylphosphine, tribenzylphosphine, 2,2'-bis(diphenylphosphinomethyl)-1,1'-biphenyl, 1,6-bis(diphenylphosphino)hexane, and the like, as well as mixtures of any two or more thereof.

Optional coordinating ligands employed in combination with the above-described bidentate organophosphines are bidentate ligands containing at least one nitrogen atom. Such bidentate ligands include 2,2'-bipyridine, a $C_1$ up to $C_6$ dialkylamino pyridine, 1,10-phenanthroline, 2-picolinic acid, polyvinyl pyridine, and the like.

When the optional use of mixtures of organophosphine and bidentate ligand containing at least one nitrogen atom as part of an aromatic ring structure are employed as the coordinating ligand, molar ratios of the organophosphine to the bidentate ligand containing at least one nitrogen atom can vary widely, for example, in the range of about 0.1:1 up to 20:1, with ratios in the range of 0.5 up to 10 preferred. Ratios in the range of about 1:1 up to 2:1 are presently most preferred because little added benefit is observed when large excesses of the bidentate ligand containing at least one nitrogen atom are employed.

The total molar ratio of coordinating ligand(s) to nickel compound employed in the practice of the present invention can vary widely. Typically, such molar ratio will fall within the range of 0.5:1 up to 20:1, with ratios in the range of 1:1 up to 10:1 preferred. Ratios in the range of about 1:1 up to 5:1 are presently most preferred because little added benefit is seen in the use of large excesses of coordinating ligand(s).

Solvents suitable for use in the practice of the present invention are typically ether-type solvents in which organometallic reagents can be readily prepared. Typical ether-type solvents suitable for use in the practice of the present invention include diethyl ether, dibutyl ether, tetrahydrofuran, 1,4-dioxane, glyme, diglyme, and the like, as well as mixtures of any two or more thereof. Optionally, substantial quantities of an aliphatic or aromatic hydrocarbon having in the range of about 5 up to 15 carbon atoms can be employed in a mixture with the ether-type solvent. The solvent system employed in the practice of the present invention should contain sufficient ether-type solvent to maintain the formed organometallic reagent substantially in solution. Up to about 95 volume percent of the solvent system can comprise such hydrocarbons. When used, preferred hydrocarbons include pentane, hexane, octane, cyclohexane, benzene, toluene, or xylene.

It is preferred that all solvents used in the practice of this invention be anhydrous.

The reaction conditions under which tertiary-alkyl organometallic reagent and aryl halide are contacted can vary widely. Typically such contacting is carried out at a temperature in the range of about 0° up to 150° C. Preferred reaction temperatures fall within the range of about 50° up to 110° C.

Similarly, reaction time employed for contacting of tertiary-alkyl organometallic reagent and aryl halide can vary widely. Suitable reaction times fall within the range of about 2 up to 48 hours or longer. Preferred reaction times fall within the range of about 4 up to 16 hours.

The molar ratio of tertiary-alkyl organometallic reagent to aryl halide employed in the practice of the present invention can vary widely. Typically, such molar ratio will fall within the range of about 0.01:1 up to 20:1, with ratios in the range of about 0.2:1 up to 10:1 preferred. Ratios in the range of about 0.9:1 up to 5:1 are presently most preferred because it is desired to minimize the quantity of alkali or alkaline earth metal species which must be removed from the reaction mixture and little added benefit is obtained when large excesses of such materials are employed.

The molar ratio of tertiary-alkyl organometallic reagent to nickel employed in the practice of the present invention can vary widely. Typically, such molar ratios will fall within the range of about 1 up to 1000:1, with ratios in the range of about 10 up to 500:1 being preferred. Ratios in the range of about 40 up to 100:1 are presently preferred for the same reasons as stated in the preceding paragraph.

Preparation of the nickel(0) compositions is carried out conveniently by mixing the aforementioned nickel compound and coordinating ligand(s) in aprotic solvent under an inert atmosphere, then adding the tertiary-alkyl organometallic reagent to the reaction mixture. The order of addition of reagents is not critical, thus other sequences of addition fall within the scope of the present invention, including combining all reagents at one time.

Reaction workup and product recovery can be carried out employing standard techniques well known by those of skill in the art.

The present invention will now be described in greater detail by reference to the following nonlimiting examples.

EXAMPLE 1

The Preparation of 2,2'-Dimethyl-1,1'-biphenyl (Standard Run)

To a nitrogen purged three neck 100 mL flask was added nickel(II) bromide (0.22 grams, 1 mmole), 2,2'-bipyridine (0.62 grams, 4 mmole), triphenylphosphine (2.62 grams, 10 mmole), 2-chlorotoluene (2.53 grams, 20 mmole) and tetrahydrofuran (THF, 20 mL). The mixture was stirred at room temperature for 5 minutes and then tertiary butylmagnesiumchloride (12 mL of 2.0 Molar solution in THF, 24 mmole) was added dropwise over a 10 minute period. The reaction warmed during the addition and at the end of the addition was heated to reflux for 14 hours. The mixture was then cooled to ambient and analyzed by conventional gas chromatographic methods. The results of the reaction are:

| Conversion of 2-chlorotoluene to products | 100% |
|---|---|
| Selectivity to toluene | 7.4% |
| Selectivity to dimers | 92.6% |
| The distribution of the dimer fraction is: | |
| Biphenyl | 1.2% |
| Methyl Biphenyl | 6.6% |
| 2,2'-Dimethyl-1,1'-biphenyl | 91.4% |
| Isomeric Bitolyls | 0.8% |

EXAMPLE 2

The Preparation of 2,2'-Dimethyl-1,1'-biphenyl (Inverse Addition Run)

To a nitrogen purged three neck 100 mL flask was added nickel(II) bromide (0.22 grams, 1 mmole), 2,2'-bipyridine (0.62 grams, 4 mmole), triphenylphosphine (2.62 grams, 10 mmole), and tetrahydrofuran (20 mL). The mixture was stirred at room temperature for 5 minutes and then tertiary-butylmagnesium chloride (12 mL of 2.0 Molar solution in THF, 24 mmole) was added as a single portion. The reaction changed from a reddish brown suspension into a deep red homogenous solution and warmed slightly. The reaction was stirred for 5 minutes and then 2-chlorotoluene (2.53 grams, 20 mmole) was added dropwise over a 5 minute period. Upon completion of the addition, the reaction was heated to reflux for 14 hours. The mixture was cooled to ambient and analyzed by conventional gas chromatographic methods. The results of the reaction are:

| Conversion of 2-chlorotoluene to products | 99.8% |
|---|---|
| Selectivity to toluene | 7.3% |
| Selectivity to dimers | 92.7% |
| The distribution of the dimer fraction is: | |
| Biphenyl | 2.4% |
| Methyl Biphenyl | 6.8% |
| 2,2'-Dimethyl-1,1'-biphenyl | 89.2% |
| Isomeric Bitolyls | 1.6% |

EXAMPLE 3

The Preparation of 2,2'-Dimethyl-1,1'-biphenyl With In Situ Formation of Grignard Reagent To a nitrogen purged three neck 100 mL flask was charged magnesium turnings (0.97 grams, 40 mmole), 2-chlorotoluene (2.53 grams, 20 mmole), anhydrous nickel(II) bromide (0.22 grams, 1 mmole), triphenylphosphine (0.52 grams, 2 mmole), 2.2'-bipyridine (0.62 grams, 4 mmole) and THF (40 mL). The mixture was heated to reflux and then tertiary butylchloride (3.7 grams, 40 mmole) was added. Approximately 25 percent of the butyl chloride was added as a single portion and the reaction refluxed until the Grignard reagent formation initiated. The remainder of the butyl chloride was added dropwise over a 5-minute period. The reaction was then refluxed for 16 hours, cooled to ambient, and analyzed by conventional gas chromatographic methods. Analysis of the mixture showed:

| Conversion of 2-chlorotoluene to products | 100% |
|---|---|
| Selectivity to toluene | 41.9% |
| Selectivity to dimers | 58.1% |
| The distribution of the dimer fraction is: | |
| Biphenyl | 2.0% |
| Methyl Biphenyl | 14.9% |
| 2,2'-Dimethyl-1,1'-biphenyl | 82.1% |
| Isomeric Bitolyls | 1.0% |

EXAMPLE 4

The Preparation of 2,2'-Dimethyl-1,1'-biphenyl Using Polyvinylpyridine as Nitrogen Ligand To a nitrogen purged three-neck 100 mL flask was added nickel(II) bromide (0.22 grams, 1 mmole), polyvinyl pyridine (0.63 grams of Reillex ® 402 obtained from Reilly Tar and Chemical Company, Indianapolis, IN), triphenylphosphine (2.62 grams, 10 mmole), 2-chlorotoluene (2.53 grams 20 mmole) and tetrahydrofuran (20 mL). The mixture was stirred at room temperature for 5 minutes and then tertiary-butyl-magnesium chloride (12 mL of 2.0 Molar solution in THF, 24 mmole) was added dropwise over a 10 minute period. The reaction warmed upon addition and at the end of the addition was heated to reflux for 14 hours. The mixture was cooled to ambient and analyzed by conventional gas chromatographic methods. The results of the reaction are:

| Conversion of 2-chlorotoluene to products | 97.4% |
|---|---|
| Selectivity to toluene | 51.8% |
| Selectivity to dimers | 48.2% |
| The distribution of the dimer fraction is: | |
| Biphenyl | 3.2% |
| Methyl Biphenyl | 5.6% |
| 2,2'-Dimethyl-1,1'-biphenyl | 87.3% |
| Isomeric Bitolyls | 3.9% |

EXAMPLE 5

The Preparation of 2,2'-Dimethyl-1,1'-biphenyl Using Phosphine Ligands

All of the following runs were made with 1 mmol NiBr$_2$, an organophosphine (as designated in Table I), 4 mmol 2,2'-bipyridine, 20 mmol 2-chlorotoluene, 24 mmol tertiary-butylmagnesium chloride in 20 mL THF for 16 hours at reflux.

Table 1 illustrates the successful use of bidentate phosphine ligands, trialkyl phosphines, diphenylalkyl phosphines and triaryl phosphines in conjuction with 2,2'-bipyridine for the successful coupling of aryl halides.

TABLE 1

Effectiveness of Various Types of Phosphine Ligands

| Organo Phosphine | mmol ligand | Percent Conv. | Selectivity | | Dimer Distribution | | | |
|---|---|---|---|---|---|---|---|---|
| | | | Toluene | Dimers | Ph—Ph | CH$_3$—PhPh | Bitolyl | Isomers |
| Triphenyl | 10.0 | 100.0 | 7.4 | 91.4 | 1.2 | 6.6 | 91.4 | 0.8 |
| BISBI | 4.0 | 84.4 | 21.2 | 78.8 | 1.0 | 4.8 | 93.4 | 0.9 |
| BISBI | 1.5 | 87.6 | 17.1 | 82.9 | 0.8 | 4.0 | 94.4 | 0.8 |
| Tributyl | 4.0 | 90.5 | 56.1 | 43.9 | 0.0 | 0.0 | 98.1 | 1.9 |

TABLE 1-continued

Effectiveness of Various Types of Phosphine Ligands

| Organo Phosphine | mmol ligand | Percent Conv. | Selectivity | | Dimer Distribution | | | |
|---|---|---|---|---|---|---|---|---|
| | | | Toluene | Dimers | Ph—Ph | $CH_3$—PhPh | Bitolyl | Isomers |
| Diphenyl-butyl | 6.0 | 100.0 | 17.8 | 82.2 | 1.3 | 1.8 | 95.7 | 1.4 |
| BDPPB | 2.0 | 36.8 | 93.2 | 6.8 | 53.6 | 2.6 | 43.8 | 0.0 |
| OXYL | 1.5 | 40.0 | 100 | 0.0 | | | | |
| BDPPH | 1.5 | 97.9 | 8.4 | 91.6 | 0.5 | 1.8 | 96.4 | 1.3 |
| BDPPF | 1.5 | 76.3 | 27 | 73 | 1.2 | 2.1 | 95.6 | 1.1 |
| DIPHOS | 1.5 | 20.2 | 95.7 | 4.3 | 84.7 | 0 | 15.3 | 0 |

BISBI = 2,2'-Bis(diphenylphosphinomethyl)-1,1'-biphenyl
BDPPB = 1,4-Bis(diphenylphosphine)butane
OXYL = Bis(alpha,alpha'-diphenylphosphino)-o-xylene
BDPPH = 1,6-Bis(diphenylphosphino)hexane
BDPPF = 1,1'-Bis(diphenylphosphino)ferrocene
DIPHOS = 1,2-Bis(diphenylphosphino)ethane

EXAMPLE 6

The Preparation of 2,2'-Dimethyl-1,1'-biphenyl Using Nitrogen Ligands

All of the following runs were made with 1 mmol $NiBr_2$ and 24 mmol t-butylmagnesium chloride in THF at reflux for 16 hours. Protic ligands were converted to their magnesium salts by the addition of an equivalent amount of a Grignard reagent prior to addition of 2-chlorotoluene.

Table 2 illustrates the operability of various types of nitrogen ligands which were examined in the course of this work. The presently preferred lignads are 2,2'-bipyridine and 1,10-phenanthroline.

TABLE 2

Nitrogen Ligand Effects on the t-Butylmagnesium Chloride Promoted Aryl Coupling Reaction

| Nitrogen Ligand | % Conv. 2-CT | Selectivity | | % Desired Isomer |
|---|---|---|---|---|
| | | Toluene | Dimers | |
| Bipyridine | 100 | 7.4 | 92.6 | 91.4 |
| PHEN | 90 | 26.9 | 73.1 | 85 |
| PICA | 90 | 49.1 | 50.9 | 88 |
| PYRDA | 100 | 49.6 | 50.4 | 87.2 |
| None | 99.2 | 57.2 | 31.7 | 83.6 |
| LUTD | 94.8 | 57.9 | 42 | 89.3 |
| TMEDA | 100 | 60.5 | 39.5 | 91.5 |
| SALEN | 76.9 | 63.5 | 36.5 | 86.9 |
| EDTA | 98.3 | 68.8 | 31.2 | 86.9 |
| Pyridine | 60 | 68.9 | 30.4 | 83.9 |

PEN = 1,10 Phenanthroline
PICA = Picolinic Acid (magnesium salt)
PYRDA = 2,6-Pyridine dicarboxylic acid (magnesium salt)
LUTD = 2,6-Lutidine
TMEDA = Tetramethyl ethylene diamine
SALEN = N,N'-Bis(salicylidene)ethylenediamine (magnesium salt)
EDTA = Ethylene diamine tetraacetic acid (magnesium salt)

The invention has been described in detail with particular reference to preferred embodiments thereof, but it will be understood that variations and modifications can be effected within the spirit and scope of the invention.

I claim:

1. A method for the generation of nickel (0) species from nickel (II) compounds comprising contacting a nickel (II) compound with
   (i) an organophosphine ligand of the formula $PR''_3$ or $R''_2P$-Z-$PR''_2$ wherein each R'' is independently selected from the group consisting of alkyl, aryl and alkaryl radicals having up to 20 carbon atoms and -Z- is an alkylene, alkenylene, or arylene radical;
   (ii) a bidentate ligand selected from the group consisting of 2,2'-bipyridine, 2-picolinic acid, ethylenediamine tetraacetic acid, N,N,N',N'-tetramethylethylenediamine, 1,10-phenanthroline, N,N'-bis(salicylidene)ethylenediamine, and polyvinyl pyridine;
   (iii) a tertiary-alkyl organometallic compound of the structure:

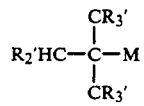

wherein each R' is independently selected from the group consisting of H and alkyl groups having in the range of 1 up to 20 carbon atoms, and M is selected from the group consisting of Li, Na, K, and MgX, wherein X is a halogen;
wherein said contacting is carried out in a substantially anhydrous, non-polar, ethereal solvent system, optionally containing up to 95 volume percent of an aliphatic or aromatic hydrocarbon diluent at a temperature in the range of about 0° up to 100° C. for a time in the range of about 0.5 up to 24 hours.

2. A method for the generation of nickel (0) species from nickel (II) compounds comprising contacting a nickel (II) compound with
   (i) an organophosphine ligand of the formula $PR''_3$ or $R''_2P$-Z-$PR''_2$ wherein each R'' is independently selected from the group consisting of alkyl, aryl and alkaryl radicals having up to 20 carbon atoms and -Z- is an alkylene, alkenylene, or arylene radical;
   (ii) a bidentate ligand selected from the group consisting of 2,2'-bipyridine, 2-picolinic acid, ethylenediamine tetraacetic acid, N,N,N',N'-tetramethylethylenediamine, 1,10-phenanthroline, N,N'-bis(salicylidene)ethylenediamine, and polyvinyl pyridine; and
   (iii) a tertiary-alkyl halide of the structure:

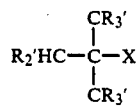

wherein each R' is independently selected from the group consisting of H and alkyl groups having in the range of 1 up to 20 carbon atoms, and X is a halogen; and (iv) a metal, M, selected from the groups consisting of Li, Na, K or Mg;

wherein said contacting is carried out in a substantially anhydrous, non-polar, ethereal solvent system, optionally containing up to 95 volume percent of an aliphatic or aromatic hydrocarbon diluent at a temperature in the range of about 0° up to 100° C. for a time in the range of about 0.5 up to 24 hours.

3. A process in accordance with claim 1 wherein said nickel (II) compound is selected from the group consisting of nickel acetylacetonate, nickel sulfate, nickel nitrate, nickel oxide, the nickel hydroxides, the nickel halides, and the nickel carboxylates.

4. A process in accordance with claim 1 wherein said organophosphine ligand is selected from the group consisting of triphenylphosphine, tricyclohexylphosphine, tribenzylphosphine, diphenylbutylphosphine, 1,4-bis(diphenylphosphino)butane, 1,6-bis-(diphenylphosphino)hexane, 1,1'-bis(diphenylphosphino)ferrocene, 2,2'-bis(-diphenylphosphinomethyl)-1,1'-biphenyl, bis($\alpha,\alpha'$-diphenylphosphino)-o-xylene, and 1,2-bis(diphenylphosphino)ethane.

5. A process in accordance with claim 1 wherein said tertiary-alkyl organometallic compound is selected from the group consisting of t-butylmagnesium chloride, t-butyl lithium, t-butyl sodium, t-butyl potassium, t-amylmagnesium chloride, t-amyl lithium, t-amyl sodium, and t-amyl potassium.

6. A process in accordance with claim 1, wherein the molar ratio of tertiary-alkyl organometallic compound to nickel falls in the range of about 0.2:1 up to 5:1.

7. A process in accordance with claim 1 wherein the molar ratio of nitrogen-containing ligand to nickel falls in the range of about 0.5:1 up to 20:1.

8. A process in accordance with claim 1 wherein the molar ratio of organophosphine to nickel falls in the range of about 0.3:1 up to 30:1.

9. A process in accordance with claim 1 wherein said solvent system comprises at least one ether selected from the group consisting of dimethyl ether, tetrahydrofuran, diisopropyl ether, dibutyl ether, ethylene glycol dimethyl ether, dioxane, and methyl t-butyl ether, and, optionally, up to 95 volume % of an aliphatic or aromatic hydrocarbon selected from the group consisting of benzene, toluene, xylene, hexane, octane, cyclohexane, and mixtures of any two or more thereof.

* * * * *